United States Patent [19]

Potempa

[11] Patent Number: 5,405,832
[45] Date of Patent: Apr. 11, 1995

[54] METHOD OF TREATING NON-STREPTOCOCCAL BACTERIAL INFECTIONS

[75] Inventor: Lawrence A. Potempa, Deerfield, Ill.

[73] Assignee: Immtech International Inc., Evanston, Ill.

[21] Appl. No.: 800,508

[22] Filed: Nov. 27, 1991

[51] Int. Cl.⁶ .................. C07K 15/28; C12N 5/12; G01N 33/53
[52] U.S. Cl. ........................................... 514/12; 514/8
[58] Field of Search ................... 514/8, 12; 435/7.92

[56] References Cited

U.S. PATENT DOCUMENTS

5,272,258  12/1993  Siegel et al. ................... 530/388.25

FOREIGN PATENT DOCUMENTS

WO89/09628  10/1989  WIPO .

OTHER PUBLICATIONS

Ballou et al., *J. Lab. Clin. Med.*, 115, 332–338 (1990).
Barna et al., *Cancer Research*, 44, 305–310 (1984).
Bray et al., *Clin. Immunol. Newsletter*, 8, 137–140 (1987).
Chu et al., *Proc. Amer. Acad. Cancer Res.*, 28, 344a (1987).
Chu et al., *Proc. Amer. Acad. Cancer Res.*, 29, 371a (1988).
Chudwin et al., *J. Allergy Clin. Immunol.*, 77, 216a (1986).
Deodhar et al., *Cancer Research*, 42, 5084–5088 (1982).
Galanos et al., *Proc. Natl. Acad. Sci. USA*, 76, 5939 (1979).
Gotschlich, *Ann. N.Y. Acad. Sci.*, 557, 9–18 (1989).
Gupta et al., *J. Immunol.*, 137, 2173–2179 (1986).
Hokama et al., *J. Bacteriology*, 83, 1017–1024 (1962).
Horowitz et al., *J. Immunol.*, 138, 2598–2603 (1987).
Hu et al., *J. Biol. Chem.*, 263, 1500–1504 (1988).
Hu et al., *Biochem.*, 25, 7834–7839 (1986).
James et al., *Dissertation Abstracts International*, 41/08-B, 2963 (1980).
Kempka et al., *J. Immunol.*, 144, 1004–1009 (1990).
Kilpatrick and Volanakis, *Immunol. Res.*, 10, 43–53 (1991).
Kilpatrick and Volanakis, *J. Immunol.*, 134, 3364–3370 (1985).
Kindmark, *Clin. Exp. Immunol.*, 8, 941–948 (1971).
Lei et al., *J. Biol. Chem.*, 260, 13377–13383 (1985).
Mantzouranis et al., *Ped. Res.*, 18, 260a (1984).
Mitzner et al., *Artificial Organ*, 15, 338 (1991).
Mold et al., *Ann. N.Y. Acad. Sci.*, 389, 251–262 (1982).
Mold et al., *Infection and Immunity*, 38, 392–395 (1982).
Nagaki et al., *Artificial Organ*, 15, 338 (1991).
Nakayama et al., *Clin. Exp. Immunol.*, 54, 319–326 (1983).
Nakayama et al., *J. Immunol.*, 132, 1336–1340 (1984).
Nanbu et al., *Artificial Organ*, 15, 290 (1991).
Noronha-Blob et al., *Eur. J. Pharmacol.*, 199, 387–388 (1991).
Potempa et al., *Protides Biol. Fluids*, 34, 287–290 (1986).
Potempa et al., *Mol. Immunol.*, 24, 531–541 (1987).
Potempa et al., *Inflammation*, 12, 391–405 (1988).
Potempa et al., *Mol. Immunol.*, 20, 1165–1175 (1983).
Potempa et al., *FASEB J.*, 2, 731a (1988).
Potempa et al., *Proc. Amer. Acad. Cancer Res.*, 28, 344a (1987).
Rees et al., *Fed. Proc.*, 45, 263a (1986).
Samols et al., *Biochem. J.*, 227, 759–765 (1985).
Samola and Hu, *Protides Biol. Fluids*, 34, 263–266 (1986).

(List continued on next page.)

Primary Examiner—Howard E. Schain
Assistant Examiner—Phynn Touzeau
Attorney, Agent, or Firm—Willian Brinks Hofer Gilson & Lione

[57] ABSTRACT

A method of treating non-Streptococcal bacterial infections in a mammal comprising administering to the mammal an effective amount of modified C-reactive protein (CRP) in a pharmaceutically-acceptable carrier. Modified-CRP has been found to be particularly effective in treating gram-negative bacterial infections and endotoxic shock.

12 Claims, No Drawings

OTHER PUBLICATIONS

Tebo et al., *J. Immunol.*, 144, 231–238 (1990).
Teng et al., *Proc. Natl. Acad. Sci. USA*, 82, 1790–1794 (1985).
Thombre et al., *Cancer Immunol. Immunother.*, 16, 145–150 (1984).
Tillett and Francis, *J. Exp. Med.*, 52, 561–571 (1930).
Volanakis, et al., *J. Immunol.*, 113, 9–17 (1974).
Whitehead et al., *Biochem. J.*, 266, 283–290 (1990).
Woo et al., *J. Biol. Chem.*, 260, 13384–13388 (1985).
Xia et al., *FASEB J.*, 5, A1628 (1991).
Ying et al., *J. Immunol.*, 143, 221–228 (1989).
Zeller et al., *Fed. Proc.*, 46, 1033a (1987).
Ziegler et al., *New Eng. J. Med.*, 324, 429–435 (1991).
Ziegler et al., *Clin. Res.*, 35, 619A (1987).
Bacterial Endotoxic Lipopolysaccharides, vol. II, Immunopharmacology as Pathophysiology, ed by J. L. Ryan ad D. C. Morrison, CRC Press, Boca Raton.
F. B. Taylor, Jr., Baboon Model of E. Coli Seplsis: Summary . . . Marbers, #42, Collogiom, Mosbach '91 Molecular Aspects of Inflammation, Springer–Verlag, Berlin, 1991.
Ammar et al. J. Clin. Invest., 87(6) 2048–2055 Biological and Biochemical . . . normal T Cells.
Rudd et al, PNAS, 85 pp. 5190–5194 Jul. '88, The C04 Receptor . . . T lymphocytes.

METHOD OF TREATING NON-STREPTOCOCCAL BACTERIAL INFECTIONS

FIELD OF INVENTION

This invention relates to a method of treating non-Streptococcal bacterial infections with modified C-reactive protein.

BACKGROUND

Septicemia (or sepsis) is a leading cause of morbidity and mortality among hospitalized patients. Ziegler et al., *New Eng. J. Med.*, 324, 429–35 (1991). There are approximately 400,000 cases each year in the United States, and the incidence continues to increase. Id. Gram-negative bacteremia occurs in about 30% of patients with septicemia. Id. Despite the use of antibiotics and intensive care, the mortality among patients with sepsis and gram-negative bacteremia remains as high as 20–60% depending on the specific population. Id.

Bacteremia and septic shock are associated with the release of endotoxins into the circulation. Id. Endotoxins are the lipopolysaccharide components of the outer membranes of gram-negative bacteria that trigger many of the adverse systemic reactions and serious sequelae in patients with sepsis and gram-negative bacteremia. Id. Endotoxins consist of a polysaccharide portion and a lipid portion (lipid A). The polysaccharide portion contains species-specific (O chain) and group-specific (core) components, i.e. the composition of the core is common to one group of bacteria, whereas the O chain varies from species to species within a genus. For instance, more than 1000 species-specific serotypes of Salmonella have been characterized for one core component. The lipid A moiety is common to all endotoxins and is primarily responsible for the toxicity of endotoxins.

Human polyclonal antiserum specific for endotoxin has been shown to reduce mortality in patients with gram-negative bacteremia and to protect high-risk surgical patients from septic shock. Id. This antiserum was developed by immunizing volunteers with heat-inactivated cells of the J5 mutant of *Escherichia coli* 0111:B4 which induced an immune response to the core region of endotoxin. The article states that this region is shared among gram-negative bacterial species and contains lipid A.

A human monoclonal antibody (HA-1A) specific for the lipid A domain of endotoxin has been successfully tested in animal models of gram-negative bacteremia and endotoxemia. Ziegler et al., *New Eng. J. Med.*, 324, 430 (1991); Teng et al., *Proc. Natl. Acad. Sci. USA*, 82, 1790–94 (1985); Ziegler et al., *Clin. Res.*, 35, 619A (1987). HA-1A has been shown to bind specifically to many endotoxins and to a broad range of clinical isolates of gram-negative bacteremia. Ziegler et al., *New Eng. J. Med.*, 324, 430 (1991).

The results of a large double-blind, placebo-controlled trial of the HA-1A monoclonal antibody were reported in Ziegler et al., *New Eng. J. Med.*, 324, 429–435 (1991). Of 200 patients with gram-negative bacteremia proved by blood culture, 105 patients received the HA-1A antibody and 92 patients received placebo. Among the patients receiving the antibody, the mortality rate was 30% over a 28 day period; among patients receiving placebo, the mortality rate was 49%. No benefit from treatment with HA-1A was demonstrated in an additional 343 patients with sepsis who did not prove to have gram-negative bacteremia.

NPC 15669 (N-[9H-(2,7-dimethylfluoren-9-ylmethoxy)carbonyl]-L-leucine) is an anti-inflammatory agent. Noronha-Blob et al., *Eur. J. Pharmacol.*, 199, 387–88 (1991) recently reported that NPC 15669 could reverse endotoxin-mediated leukopenia and reduce mortality from endotoxic shock in mice. Mice pretreated with NPC 15669 two hours prior to a lethal dose of endotoxin "were afforded complete protection (100% survival)." Id. at 387. The authors suggest that NPC 15669 may be of significant therapeutic value in the treatment of septic shock.

Others have tried to control or avoid the effects of endotoxins by using endotoxin-binding adsorbents to remove endotoxins from blood, plasma, and other fluids. See Mitzner et al., *Artficial Organ*, 15, 338 (1991); Nagaki et al., *Artificial Organ*, 15, 338 (1991); Nanbu et al., *Artificial Organ*, 15, 290 (1991). Such endotoxin-binding adsorbents are particularly important in dialysis procedures.

C-reactive protein (CRP) was first described by Tillett and Francis [*J. Exp. Med.*, 52, 561–71 (1930)] who observed that sera from acutely ill patients precipitated with fraction C of the cell wall of *Streptococcus pneumoniae*. Others subsequently identified the reactive serum factor as protein, hence the designation "C-reactive protein."

In addition to binding to pneumococcal C-polysaccharide, CRP binds to: 1) phosphate monoesters, including particularly phosphorylcholine; 2) other cell wall polysaccharides containing phosphorylcholine; 3) phosphatidyl choline (lecithin); 4) fibronectin; 5) chromatin; 6) histones; and 7) the 70 kDa polypeptide of the U1 small nuclear ribonucleoprotein. Kilpatrick and Volanakis, *Immunol. Res.*, 10, 43–53 (1991). Several laboratories have also reported the binding of CRP to galactose-containing polysaccharides. Id. However, one laboratory has reported that CRP binds to trace phosphate groups that are minor constituents of one particular galactan, making it is unclear whether CRP binding to other galactans is also directed to phosphate residues or to carbohydrate determinants. Id.

Xia et al., *FASEB J.*, 5, A1628 (1991) describes experiments designed to explore the role of CRP in endotoxin shock. A chimeric gene coding for rabbit CRP under the control of an inducible promoter (inducible in response to demand for gluconeogenesis) was introduced into mice. In contrast to most other vertebrates, mice synthesize only trace amounts of endogenous CRP, even during an acute phase response. When the chimeric gene was introduced into mice, rabbit CRP was expressed in response to demand for gluconeogenesis. Further, it was found that 75% of mice expressing high levels of rabbit CRP following induction of gluconeogenesis survived treatment with 350–400 μg of endotoxin, as compare to 27% survival for animals in which rabbit CRP synthesis had been suppressed by inhibiting gluconeogenesis. The authors speculate that CRP may play a role in natural defense against endotoxin shock, although CRP is not known to bind endotoxin.

Mold et al., *Infection and Immunity*, 38, 392–395 (1982) reports that CRP binding can lead to complement activation and, in the presence of complement, enhancement of opsonization of C-polysaccharide-sensitized erythrocytes and type 27 *S. pneumoniae*. The article further reports that injection of CRP increased survival in mice challenged with type 3 or type 4 *S.*

*pneumoniae*. Finally, the authors describe test results from which they conclude that CRP binds to a small group of potentially pathogenic gram-positive bacteria (*S. pneumoniae, Streptococcus viridans,* and one isolate of *Staphylococcus aureus*), but does not bind to gram-negative bacteria or to other gram-positive bacteria. They, therefore, postulate that the ability of CRP to enhance opsonization and contribute to host defense may be specific for infection with *S. pneumoniae*.

Similarly, Mold et al., *Ann. N.Y. Acad. Sci.,* 389, 251–62 (1982) reports that CRP can act as an opsonin in the presence of complement. However, the article teaches that CRP does not bind to gram-negative bacteria and binds to only some gram-positive organisms. For those gram-positive bacteria to which CRP binds, the effectiveness of CRP as an opsonin varied depending on the species. Finally, the article reports that CRP protected mice from *S. pneumoniae* infection.

Nakayama et al., *Clin. Exp. Immunol.,* 54, 319–26 (1983) also teaches that CRP protects against lethal infection with type 3 or type 4 *S. pneumoniae*. The article further teaches that CRP did not protect against a similar dose of *Salmonella typhimurium* LT2.

Horowitz et al., *J. Immunol.,* 138, 2598–2603 (1987) describes the effects of CRP in mice with a X-linked immunodeficiency ("xid mice") which prevents the mice from making antibodies to polysaccharide antigens. In these mice, CRP provided protection against infection with type 3 *S. pneumonia* and acted by clearing the bacteria from the blood. However, CRP was not completely protective at higher doses of *S. pneumoniae*. Since CRP provides complete protection against these doses in normal mice, the authors speculated that CRP's function is to slow the development of pneumococcal bacteremia until protective antibodies to capsular polysaccharide can be produced. C3 depletion decreased or abrogated the protective effects of CRP in xid mice, but not in normal mice.

Nakayama et al., *J. Immunol.,* 132, 1336–40 1984) reports the results of injecting mice with 50–200 μg of CRP and then immunizing them with type 3 *S. pneumococci*. The result was a diminished antibody response to the phosphorylcholine determinants on the bacteria which varied with the dose of CRP. However, antibodies were formed to other antigenic determinants on the *S. pneumococci*.

Hokama et al., J. Bacteriology, 83, 1017–1024 (1962) reports that carbonyl iron spherules, *Diplococcus pneumoniae* types IIs and XXVIIs and *Serratia marcescens* were phagocytosed more rapidly and in greater numbers by leukocytes of normal human blood after incubation with CRP. Similarly, Kindmark, *Clin. Exp. Immunol.,* 8, 941–48 (1971) reports that CRP stimulated phagocytosis of *Diplococcus pneumoniae, Staphylococcus aureus, Escherichia coli* and *Klebsiella aerogenes*.

Gupta et al., *J. Immunol.,* 137, 2173–79 (1986) teaches that CRP has been detected in immune complexes isolated from the sera of patients with acute rheumatic fever. Rheumatic fever is an acute inflammatory disease that may follow group A streptococcal pharyngitis. The other components of the immune complexes included streptolysin O and antibodies to streptolysin O.

However, Ballou et al., *J. Lab. Clin. Med.,* 115, 332–38 (1990) teaches that highly purified CRP does not bind to immunoglobulin (monomeric or aggregated) or immune complexes. The article suggests that the reported presence of CRP in immune complexes may result from, or be facilitated by, an association of CRP with components of the immune complexes other than immunoglobulin, such as antigens or complement components.

Kilpatrick and Volanakis, *J. Immunol.,* 134, 3364–70 (1985) reports that there is a CRP receptor on stimulated polymorphonuclear leukocytes (PMN). The authors also disclose that the ingestion of erythrocytes coated with pneumococcal C-polysaccharide and CRP by activated PMN is greater than ingestion of erythrocytes coated only with pneumococcal C-polysaccharide. Finally, the authors propose that CRP's function relates to its ability to specifically recognize foreign pathogens and damaged or necrotic host cells and to initiate their elimination by 1) interacting with the complement system or 2) interacting with inducible phagocytic receptors on neutrophils.

James et al., *Dissertation Abstracts International,* 41/08-B, 2963 (1980) teaches that CRP binds to a subset of mononuclear leukocytes, including 40% of the phagocytic monocytes and 3% of lymphocytes. Binding was influenced by several factors, including the form of the CRP molecule (i.e., modification of the CRP was required, either by complexing to a ligand or by heating to 63° C).

Tebo et al., *J. Immunol.,* 144, 231–38 (1990) teaches the presence of a receptor for CRP on monocytes. The article further discloses that a membrane receptor for CRP has been reported on neutrophils.

Kempka et al., *J. Immunol.,* 144, 1004–1009 (1990) discloses results which the authors interpret to mean that CRP is a galactose-specific binding protein which, when associated to the surface of liver macrophages, functions as a receptor mediating galactose-specific endocytosis of particulate ligands.

CRP is a pentamer which consists of five identical subunits. The pentameric form of CRP is sometimes referred to as "native CRP." In about 1983, another form of CRP was discovered which is referred to as "modified-CRP" or "mCRP". mCRP has significantly different charge, size, solubility and antigenicity characteristics as compared to native CRP. Potempa et al., *Mol. Immunol.,* 20, 1165–75 (1983). In particular, mCRP has a pI of 5.4, alpha globulin electrophoretic mobility and a molecular weight of about 22,000 in contrast to native CRP which has a pI of 6.4, gamma globulin electrophoetic mobility and a molecular weight of about 110,000. Id.; Potempa et al., *Molec. Immunol.,* 24, 531–41 (1987). Also, mCRP has limited solubility and tends to aggregate in buffers of ionic strength 0.15, but remains soluble when the ionic strength is reduced to 0.015. Id. mCRP also differs from native CRP in binding characteristics; for instance, mCRP does not bind phosphorylcholine. Potempa et al., *Molec. Immunol.,* 20, 1165–75 (1983); Chudwin et al., *J. Allergy Clin. Immunol.,* 77, 216a (1986). Finally, mCRP differs from native CRP in its biological activity. See Potempa et al., *Protides Biol. Fluids,* 34, 287–290 (1986); Potempa et al., *Inflammation,* 12, 391–405 (1988).

The distinctive antigenicity of mCRP has been referred to as "neo-CRP." Neo-CRP antigenicity is expressed on:

1) CRP treated with acid, urea or heat under certain conditions (described below);

2) the primary translation product of DNA coding for CRP (preCRP); and

3) CRP immobilized on plastic surfaces. Potempa et al., *Mol. Immunol.,* 20, 1165–75 (1983); Mantzouranis et al., *Ped. Res.*, 18, 260a (1984); Samols et al., *Biochem. J.*, 227, 759–65 (1985); Chudwin et al., *J. Allergy Clin. Immunol.*, 77, 216a (1986); Potempa et al., *Inflammation*, 12, 391–405 (1988).

A molecule reactive with polyclonal antibody specific for neo-CRP has been identified on the surface of 10–25% of peripheral blood lymphocytes (predominantly NK and B cells), 80% of monocytes and 60% of neutrophils, and at sites of tissue injury. Potempa et al., *FASEB J.*, 2, 731a (1988); Bray et al., *Clin. Immunol. Newsletter*, 8, 137–140 (1987); Rees et al., *Fed. Proc.*, 45, 263a (1986). In addition, it has been reported that mCRP can influence the development of monocyte cytotoxicity, improve the accessory cell function of monocytes, potentiate aggregated-IgG-induced phagocytic cell oxidative metabolism, and increase the production of interleukin-1, prostaglandin E and lipoxygenase products by monocytes. Potempa et al., *Protides Biol. Fluids*, 34, 287–290 (1987); Potempa et al., *Inflammation*, 12, 391–405 (1988); Chu et al., *Proc. Amer. Acad. Cancer Res.*, 28, 344a (1987); Potempa et al., *Proc. Amer. Acad. Cancer Res.*, 28, 344a (1987); Zeller et al., *Fed. Proc.*, 46, 1033a (1987); Chu et al., *Proc. Amer. Acad. Cancer Res.*, 29, 371a (1988).

Chudwin et al., *J. Allergy Clin. Immunol.*, 77, 216a (1986) teaches that mCRP can have a protective effect in mice challenged with gram-positive type 7F *S. pneumoniae*. Mice were injected intravenously with saline, native CRP, or mCRP. Thirty minutes later the mice received a lethal dose of *S. pneumoniae*. Survival at 10 days was as follows: 2/18 mice pretreated with saline; 7/12 mice pretreated with 200 µg of native CRP; 12/18 mice pretreated with 10 µg mCRP; and 5/6 mice pretreated with 100 µg of mCRP. The authors speculate that CRP may be protective against bacterial infections by mechanisms other than phosphorylcholine binding and that CRP may have a wider role in bacterial host defenses than previously suspected through mCRP (which does not bind phosphorylcholine).

To Applicant's knowledge, there have been no reports that mCRP is protective against any other kind of bacterial infection.

For a brief review of CRP and mCRP, see Gotschlich, *Ann. N.Y. Acad. Sci.*, 557, 9–18 (1989). Kilpatrick and Volanakis, *Immunol. Res.*, 10, 43–53 (1991) provides a recent review of CRP.

Finally, Applicant wishes to draw attention to certain co-pending applications on which he is named as a co-inventor. U.S. application Ser. No. 07/582,884, filed Oct. 3, 1990, relates to the use of mCRP to bind immune complexes. This application was filed as a national application of PCT application US89/01247 (published as WO 89/09628 on Oct. 19, 1989) and is a continuation-in-part of U.S. application 07/176,923, filed Apr. 4, 1988, now abandoned. Applicant is also named as a co-inventor on U.S. application Ser. No. 07/374,166, filed Jun. 29, 1989, a continuation-in-part of application Ser. No., 07/372,442 filed Jun. 27, 1989, now abandoned. This application describes and claims monoclonal antibodies selectively reactive with epitopes found on native CRP, mCRP or both Finally, being filed on even date herewith is an application entitled "Method Of Treating Viral Infections" which relates to the use of mCRP to treat such infections.

SUMMARY OF THE INVENTION

The invention provides a method of treating a non-Streptococcal bacterial infection in a mammal comprising administering to the mammal an effective amount of modified-CRP in a pharmaceutically-acceptable carrier. In particular, modified-CRP has been found effective in treating gram-negative bacterial infections and endotoxic shock.

DETAILED DESCRIPTION OF THE PRESENTLY PREFERRED EMBODIMENTS

The modified-CRP useful in the practice of the invention may be from any species. There is substantial homology between the amino acid sequences of CRP's from different species. For instance, there is from about 50 to about 80% sequence homology between CRP's from various mammalian species. Hu et al., *Biochem.*, 25, 7834–39 (1986); Whitehead et al., *Biochem. J.*, 266, 283–90 (1990); Kilpatrick and Volanakis, *Immunol. Res.*, 10, 43–53 (1991). It is, therefore, expected that mCRP from any species will be effective in treating non-Streptococcal bacterial infections. Thus, a mammal suffering from such an infection may be treated with mCRP from a different species (e.g., mice can be treated with human mCRP). Alternatively, and preferably, the mammal is treated with homologous mCRP (e.g., humans are treated with human mCRP) to avoid immune reactions to the mCRP.

mCRP is preferably made using CRP as a starting material. Methods of isolating CRP from natural sources are well known. Many such techniques are described in the references discussed in the Background section. CRP is preferably isolated from pleural or ascites fluid by calcium-dependent affinity chromatography using phosphorylcholine-substituted BioGel A 0.5m (an agarose-based resin which can be obtained from BioRad Laboratories) as described by Volanakis, et al. [*J. Immunol.*, 113, 9–17 (1978)] and modified by Potempa, et al. [*Mol. Immunol.*, 24, 531–41 (1987)]. Using this procedure, CRP can be obtained which is at least 99% pure.

Genomic and cDNA clones coding for human, mouse, and rabbit CRP have been isolated. Lei et al., *J. Biol. Chem.*, 260, 13377–83 (1985); Woo et al., *J. Biol. Chem.*, 260, 13384–88 (1985); Hu et al., *Biochem.*, 25, 7834–39 (1986); Hu et al., *J. Biol. Chem.*, 263, 1500–1504 (1988); Whitehead et al., *Biochem. J.*, 266, 283–90 (1990). Given the substantial homology between CRP's from different species, probes can readily be prepared so that genomic and cDNA clones can be isolated which code for CRP's from other species. Methods of preparing such probes and isolating genomic and cDNA clones are well known. See, e.g., Lei et al., *J. Biol. Chem.*, 260, 13377–83 (1985); Woo et al., *J. Biol. Chem.*, 260, 13384–88 (1985); Hu et al., *Biochem.*, 25, 7834–39 (1986); Hu et al., *J. Biol. Chem.*, 263, 1500–1504 (1988); Whitehead et al., *Biochem. J.*, 266, 283–90 (1990). Using one of the known clones or a newly-isolated clone, CRP can be prepared using conventional recombinant DNA techniques and cell culture and fermentation conditions. See, e.g., Hu et al., *J. Biol. Chem.*, 263, 1500–1504 (1988). However, to obtain pentameric native CRP, eukaryotic host cells, preferably mammalian host cells, should be used. See Samols and Hu, *Protides Biol. Fluids*, 34, 263–66 (1986); Hu et al., *J. Biol. Chem.*, 263, 1500–1504 (1988).

Methods of making mCRP from CRP are well known. Many such methods are described in the references discussed in the Background section.

For instance, mCRP can be prepared by denaturing CRP. CRP can be denatured by treatment with an effective amount of urea (preferably 8M) in the presence of a conventional chelator (preferably ethylenediamine tetraacetic acid (EDTA) or citric acid). Further, CRP can be treated to produce mCRP by adjusting the pH of the protein to below about 3 or above about 11-12. Finally, mCRP can be produced by heating CRP above 50° C. for a time sufficient to cause denaturation (preferably at 63° C. for 2 minutes) in the absence of calcium or in the presence of a chelator such as those listed above.

mCRP can also be prepared using recombinant DNA techniques. As noted in the Background section, the primary translation product of the CRP gene (preCRP) has been found to express neo-CRP antigenicity. Accordingly, mCRP can be prepared by selecting conditions so that that the CRP subunits are not assembled into pentameric native CRP in the host cell. This can be accomplished by expressing the desired genomic or cDNA clone in a prokaryotic host. See Samols and Hu, Prot. Biol. Fluids, 34, 263-66 (1986). The mCRP produced in this manner appears to consist of aggregates of CRP subunits and/or preCRP and perhaps other CRP peptides. See id. This form of mCRP is insoluble, and further purification is problematical. However, it should be possible to inject this insoluble material directly into mammals as a suspension without further processing since suspensions of isolated mCRP prepared from CRP have been found safe and effective when injected into mammals.

Finally, mCRP can be prepared by adsorbing CRP to hydrophobic solid surfaces. Suitable solid surfaces and conditions are described in co-pending application Ser. No. 07/582,884 and PCT application WO 89/09628, the disclosures of which are incorporated herein by reference. mCRP adsorbed to solid surfaces may be useful in removing endotoxin from fluids, such as blood, as discussed below.

mCRP may be distinguished from native CRP by several criteria. As noted in the Background section, mCRP expresses neo-CRP antigenicity, whereas native CRP does not. Neo-CRP antigenicity can be detected using polyclonal antisera specific for neo-CRP as described in the Background section. Preferably, however, mCRP is distinguished from native CRP using monoclonal antibodies like those described in Applicant's co-pending application Ser. No. 07/374,166, which has issued as U.S. Pat. No. 5,272,258, the disclosure of which is incorporated herein by reference. These monoclonal antibodies are also described in Ying et al., J. Immunol., 143, 221-28 (1989). mCRP also binds immune complexes and aggregated immunoglobulin, whereas native CRP does not, as described in Applicant's co-pending application Ser. No. 07/582,884 and published PCT application WO 89/09628. There are also several other ways to distinguish mCRP from native CRP including charge, solubility, binding characteristics and biological activity as discussed in the Background section. However, to show that a preparation contains mCRP, it is usually sufficient to establish that the preparation 1) reacts positively with an antibody specific for an epitope found only on mCRP and 2) binds aggregated immunoglobulin (e.g., aggregated IgG).

Although not wishing to be bound by any particular theory, it is believed that mCRP is formed by the dissociation of the five CRP subunits, each of which then undergoes a spontaneous conformational change to form mCRP. See Bray et al., Clin. Immunol. Newsletter, 8, 137-140 (1987). Accordingly, it is possible that fragments of the CRP subunits may have the same activities described herein as does mCRP, and the use of such fragments would come within the scope of the present invention.

It is also believed that proteins substantially homologous to CRP will have the activities described herein for mCRP, and such proteins are also considered to come within the scope of the invention. For instance, CRP subunits having a few amino acids added, deleted or substituted by, e.g., site-directed mutagenesis of the CRP gene would likely be effective in the treatment of non-Streptococcal bacterial infections and could be substituted for mCRP. In particular, mCRP is defined herein to include the primary translation product of the CRP gene.

To treat non-Streptococcal infections in a mammal, an effective amount of mCRP is administered to the mammal. The mCRP is preferably administered to the mammal before the infection becomes too serious and septic shock or endotoxic shock has developed. Most preferably, the mCRP is administered at the first indication of a non-Streptococcal bacterial infection or prophylactically to those at risk of developing non-Streptococcal bacterial infections. For instance, mCRP may be administered prophylactically to surgical patients or patients in intensive care who are at risk of developing non-Streptococcal bacterial infections. Of course, mCRP can be administered to a mammal already suffering from a non-Streptococcal bacterial infection or already suffering from septic shock or endotoxic shock.

In particular, mCRP has been found effective in treating gram-negative bacterial infections and in providing protection against the effects of endotoxin. Indeed, mCRP has been found to provide complete protection from a lethal dose of endotoxin.

mCRP will generally be administered to the mammal by injection (e.g., intravenous, intraperitoneal, subcutaneous, intramuscular) or encapsulated in liposomes. It is preferably administered by intravenous injection. mCRP may also be applied topically to, e.g., a wound or other site of infection. Finally, it should be possible to administer mCRP by means of a spray to treat respiratory infections. It should be noted that it is unlikely that mCRP can be administered orally since it is a protein.

It is understood by those skilled in the art that the dose of mCRP that must be administered will vary depending on the mammal which will receive the mCRP, the type of infection, the seriousness of the infection, the route of administration, and the identity of any other drugs being administered to the mammal. It is also understood that it may be necessary to give more than one dose of mCRP.

Effective dosages and schedules for administration of mCRP may be determined empirically, and making such determinations is within the skill of the art. Applicant has found that a dose of from about 5 $\mu$g to about 150 mg of mCRP per kg, preferably from about 250 $\mu$g to about 15 mg per kg, is effective for treating viral infections. Generally, a single dose is sufficient, but administration of mCRP should be continued until health has been restored to the mammal.

Pharmaceutically-acceptable carriers are well known. For instance, suitable carriers for the administration of mCRP include fluids such as water, saline and buffers. Preferably, phosphate buffered saline, pH 7.4, is used as the carrier. mCRP may also be administered encapsulated in liposomes [see Deodhar et al., Cancer Research, 42, 5084-5088 (1982); Thombre et al., Cancer

*Immunol. Immunother.*, 16, 145–150 (1984); Barna et al., *Cancer Research*, 44, 305–310 (1984)]. For topical application, mCRP may be incorporated into lotions, gels, cremes, etc., as is well known in the art.

mCRP may be administered alone or in combination with other drugs normally given to mammals suffering from a non-Streptococcal bacterial infection or endotoxic shock. For instance, mCRP may be administered in combination with antibiotics.

It is not known yet how mCRP exerts its anti-bacterial effects. mCRP may act on the immune system of the mammal to make it more effective in coping with the bacterial infection. Alternatively, mCRP may bind to the bacteria or toxins released from the bacteria (such as endotoxin) to neutralize them. It is believed most likely that mCRP is acting in both of these ways.

If mCRP does bind to bacterial toxins, such as endotoxin, then it could be used to adsorb them from fluids such as blood, plasma, dialysis fluids, and pharmaceutical preparations. In particular, mCRP could be bound to a solid surface, such as described in co-pending application 07/582,884, and used as an adsorbent to remove such materials from fluids.

EXAMPLES

Example 1

A. Preparation Of modified-CRP

Human CRP was isolated from pleural or ascites fluid by calcium-dependent affinity chromatography using phosphorylcholine-substituted BioGel A 0.5m (an agarose-based resin obtained from BioRad Laboratories) as described by Volanakis, et al. [*J. Immunol.*, 113, 9–17 (1978)] and modified by Potempa, et al. [*Mol. Immunol.*, 24, 531–41 (1987)]. Briefly, the pleural or ascites fluid was passed over the phosphorylcholine-substituted column, and the CRP was allowed to bind. Then, the column was exhaustively washed with 75 mM Tris-HCl-buffered saline (pH 7.2) containing 2 mM $CaCl_2$ until the absorbance at 280 nanometers was less than 0.02. The CRP was eluted with 75 mM Tris, 7.5 mM citrate-buffered saline (pH 7.2). This high concentration of Tris significantly reduces non-specifically adsorbed proteins which often contaminate affinity-purified CRP preparations.

CRP-containing fractions were pooled, diluted three-fold with deionized water, adsorbed to DE52 ion exchange resin (from Whatman), and then eluted with a linear salt gradient of from 0.05M to 0.5M NaCl. CRP-containing fractions were pooled and re-calcified to 2–5 mM $CaCl_2$ (by adding a suitable amount of a 1M solution) and applied to unsubstituted Biogel A 0.5m column to remove residual serum amyloid P component (SAP).

Next, the CRP was concentrated to 1 mg/ml using ultrafiltration (Amicon; PM30 membrane) under 10–20 psi nitrogen. A CRP extinction coefficient (mg/ml) of 1.98 was used to determine concentration. Next, the concentrated CRP was exhaustively dialyzed in 10 mM Tris-HCl-buffered saline (pH 7.2) containing 2 mM $CaCl_2$, sterile-filtered and stored at 4° C. These preparations produced a single Mr 23,000 band on SDS-PAGE electrophoresis and were more than 99% free of SAP, IgG and all other proteins tested for antigenically.

To make mCRP, the CRP (prepared as described above) at 1 mg/ml was incubated in 8M ultra-pure urea (Schwartz-Mann, Spring Valley, N.Y.) in the presence of 10 mM EDTA for one hour at 37° C. The urea was removed by dialysis into 10 mM sodium phosphate buffer (pH 7.4) or Tris-HCl buffer (pH 7.2) containing 0.015M sodium chloride; more than 90% of the starting protein was accounted for in the solution phase after dialysis.

The mCRP was sterile filtered through a 0.20 micron filter (Gelman). The concentration was then adjusted to 0.5 mg/ml with 10 mM sodium phosphate buffer, pH 7.4, containing 0.015M sodium chloride to produce a solution of mCRP. This solution is referred to herein as "soluble mCRP".

Some of the sterile-filtered soluble mCRP was adjusted to physiologic ionic strength by adding sodium chloride to give a final concentration of 0.15M NaCl and then incubated in an ice bath for 15 minutes. The majority of the mCRP self-aggregated to form an opalescent solution which was centrifuged at about $5000 \times g$ for 10 minutes to sediment the protein. The sedimented protein was resuspended in an appropriate volume of sterile buffer (preferably 10 mM sodium phosphate buffer, pH 7.4, containing 0.15M NaCl) to give a final concentration of mCRP of 2–4 mg/ml. This suspension is referred to herein as "mCRP suspension".

B. Efficacy of modified-CRP In Treating Endotoxic Shock

An experiment was performed to assess the therapeutic efficacy of mCRP in an animal model of septic shock. Ten groups of 20 female CD-1 mice (Charles River Laboratories, Portage Mich.) each were injected intravenously with either:

1) 0.1 ml of a 500 μg/ml solution of soluble mCRP [i.e. 50 μg per mouse] in 10 mM sodium phosphate, 0.015M sodium chloride, pH 7.4 (prepared as described in part A); or 2) 0.1 ml of the buffer.

The mice were injected with the mCRP or buffer two hours before being injected with endotoxin in sterile, pyrogen-free 0.9% saline. Five doses of *E. coli* endotoxin 11100K235 (Ribi Immunochem Research, Inc., Hamilton, Mont.) were used, as shown in the table below. Because mouse sensitivity to endotoxin is greatly enhanced by D-galactosamine [Galanos et al., *Proc. Natl. Acad. Sci. USA*, 76, 5939 (1979)], 15 mg of D(+) galactosamine hydrochloride (Sigma Chemical, St. Louis, Mo., number 39F0539) were administered admixed with the endotoxin (total injection volume 0.5 ml). Animals were observed every six hours for 96 hours after the injection of endotoxin. The results are presented in Table 1 below.

TABLE 1

| Group | Treatment | Endotoxin (μg) | Deaths (No.) | Mortality (%) | Survival (%) |
|---|---|---|---|---|---|
| 1 | B | 0.01 | 12 | 60 | 40 |
| 2 | B | 0.05 | 17 | 85 | 15 |
| 3 | B | 0.5 | 19 | 95 | 5 |
| 4 | B | 1 | 17 | 85 | 15 |
| 5 | B | 5 | 19 | 95 | 5 |
| 6 | mCRP | 0.01 | 0 | 0 | 100 |
| 7 | mCRP | 0.05 | 0 | 0 | 100 |
| 8 | mCRP | 0.5 | 1 | 5 | 95 |
| 9 | mCRP | 1 | 0 | 0 | 100 |
| 10 | mCRP | 5 | 0 | 0 | 100 |

In TABLE 1, B = buffer.

The results show that endotoxin was generally lethal if the mice were not treated with mCRP; from 60% to 95% of the buffer-injected animals died within 12–24 hours. In contrast, only 1 of 100 animals died when pretreated with mCRP. The results were found to be significant at least at a level of p<0.005 using a chi-square test.

Example 2

Example 1 was repeated, except that the dose of mCRP was varied from 0.01 to 50 micrograms per mouse. Two doses of endotoxin were used to assure at least $LD_{90}$ (dose giving death of 90% of animals) in control groups. The two doses of endotoxin were 0.05 and 5 μg per mouse. The results are presented in Table 2 below.

TABLE 2

| GROUP | mCRP (μg) | PERCENT SURVIVAL | |
| --- | --- | --- | --- |
| | | 0.05 μg Endotoxin | 5.0 μg Endotoxin |
| 16, 17 | 0 | 5 | 0 |
| 5, 10 | 0.01 | 0 | 0 |
| 4, 9 | 0.1 | 0 | 0 |
| 3, 8 | 1 | 15 | 5 |
| 2, 7 | 5 | 75 | 85 |
| 1, 6 | 25 | 100 | 90 |
| Example 1 | 50 | 100 | 100 |

The results show that the percent survival increased as the dose of mCRP was increased. Further, chi square analysis of the data showed that the differences in survival between the control and mCRP treated groups were significant at least to the level of p<0.005.

What is claimed is:

1. A method of treating a bacterial infection in a mammal caused by a bacterium other than a *Streptococcus sp.*, the method comprising administering to the mammal an effective amount of modified-C-reactive protein (modified-CRP) in a pharmaceutically-acceptable carrier.

2. The method of claim 1 wherein the modified-CRP is administered by injection.

3. The method of claim 2 wherein the modified-CRP is administered by intravenous injection.

4. The method of claim 1 wherein the modified-CRP is administered prophylactically to the mammal.

5. A method of treating a gram-negative bacterial infection in a mammal comprising administering to the mammal an effective amount of modified-C-reactive protein (modified-CRP) in a pharmaceutically-acceptable carrier.

6. The method of claim 5 wherein the modified-CRP is administered by injection.

7. The method of claim 6 wherein the modified-CRP is administered by intravenous injection.

8. The method of claim 5 wherein the modified-CRP is administered prophylactically to the mammal.

9. A method of treating endotoxic shock in a mammal comprising administering to the mammal an effective amount of modified-C-reactive protein (modified-CRP) in a pharmaceutically-acceptable carrier.

10. The method of claim 9 wherein the modified-CRP is administered by injection.

11. The method of claim 10 wherein the modified-CRP is administered by intravenous injection.

12. The method of claim 9 wherein the modified-CRP is administered prophylactically to the mammal.

* * * * *

UNITED STATES PATENT AND TRADEMARK OFFICE
CERTIFICATE OF CORRECTION

PATENT NO.  : 5,405,832
DATED       : April 11, 1995
INVENTOR(S) : Lawrence A. Potempa It is certified that error appears in the above-indentified patent and that said Letters Patent is hereby corrected as shown below:

<u>On the Title Page</u>

Under "OTHER PUBLICATIONS", column 2, line 27, delete "Samola" and substitute --Samols--.

On page 2, under "OTHER PUBLICATIONS", column 2, line 5, delete "ad" and substitute --and--.

In column 8, lines 58-59, delete "viral infections" and substitute --non-streptococcal bacterial infections and endotoxic shock--.

Signed and Sealed this

Eighteenth Day of March, 1997

Attest:

BRUCE LEHMAN

*Attesting Officer*    *Commissioner of Patents and Trademarks*